(12) United States Patent
Boualleg et al.

(10) Patent No.: US 10,695,748 B2
(45) Date of Patent: *Jun. 30, 2020

(54) SELECTIVE HYDROGENATION CATALYST FOR A C3 HYDROCARBON CUT

(71) Applicant: IFP Energies Nouvelles, Rueil-Malmaison (FR)

(72) Inventors: Malika Boualleg, Villeurbanne (FR); Priscilla Avenier, Grenoble (FR)

(73) Assignee: IFP Energies Nouvelles, Rueil-Malmaison (FR)

(*) Notice: Subject to any disclaimer, the term of this patent is extended or adjusted under 35 U.S.C. 154(b) by 0 days.

This patent is subject to a terminal disclaimer.

(21) Appl. No.: 15/824,310

(22) Filed: Nov. 28, 2017

(65) Prior Publication Data
US 2018/0147563 A1 May 31, 2018

(30) Foreign Application Priority Data
Nov. 29, 2016 (FR) ...................... 16 61622

(51) Int. Cl.
| | | |
|---|---|---|
| *B01J 21/04* | (2006.01) | |
| *B01J 23/44* | (2006.01) | |
| *B01J 35/10* | (2006.01) | |
| *C07C 7/163* | (2006.01) | |
| *C07C 7/167* | (2006.01) | |
| *B01J 35/00* | (2006.01) | |
| *C07C 5/05* | (2006.01) | |
| *B01J 35/08* | (2006.01) | |
| *B01J 37/02* | (2006.01) | |
| *C10G 70/02* | (2006.01) | |
| *B01J 21/08* | (2006.01) | |
| *B01J 21/12* | (2006.01) | |
| *B01J 37/08* | (2006.01) | |
| *B01J 37/10* | (2006.01) | |
| *B01J 37/16* | (2006.01) | |

(52) U.S. Cl.
CPC .............. *B01J 23/44* (2013.01); *B01J 21/04* (2013.01); *B01J 21/08* (2013.01); *B01J 21/12* (2013.01); *B01J 35/002* (2013.01); *B01J 35/0006* (2013.01); *B01J 35/006* (2013.01); *B01J 35/008* (2013.01); *B01J 35/0013* (2013.01); *B01J 35/0066* (2013.01); *B01J 35/08* (2013.01); *B01J 35/109* (2013.01); *B01J 35/1014* (2013.01); *B01J 35/1019* (2013.01); *B01J 35/1038* (2013.01); *B01J 35/1042* (2013.01); *B01J 35/1047* (2013.01); *B01J 35/1061* (2013.01); *B01J 37/0211* (2013.01); *B01J 37/0213* (2013.01); *B01J 37/0236* (2013.01); *B01J 37/08* (2013.01); *B01J 37/10* (2013.01); *B01J 37/16* (2013.01); *C07C 5/05* (2013.01); *C07C 7/163* (2013.01); *C07C 7/167* (2013.01); *C10G 70/02* (2013.01); *C07C 2521/04* (2013.01); *C07C 2523/44* (2013.01); *Y02P 20/52* (2015.11)

(58) Field of Classification Search
CPC ... B01J 21/04; B01J 21/06; B01J 21/08; B01J 21/12; B01J 23/44; B01J 35/0006; B01J 35/10
See application file for complete search history.

(56) References Cited

U.S. PATENT DOCUMENTS

| | | | | |
|---|---|---|---|---|
| 4,230,897 A | * | 10/1980 | Cosyns .................... | B01J 23/44 585/260 |
| 4,347,392 A | | 8/1982 | Cosyns | |
| 4,493,906 A | * | 1/1985 | Couvillion ............... | B01J 23/72 502/346 |
| 4,940,687 A | * | 7/1990 | Liu .......................... | B01J 21/04 502/325 |
| 6,350,717 B1 | * | 2/2002 | Frenzel .................... | B01J 23/44 502/327 |
| 2005/0137433 A1 | | 6/2005 | Bergmeister | |
| 2010/0125158 A1 | * | 5/2010 | Negiz ....................... | C07C 5/05 585/260 |
| 2010/0197488 A1 | * | 8/2010 | Hagemeyer ................ | B01J 2/16 502/242 |
| 2010/0236986 A1 | * | 9/2010 | Fischer .................... | B01J 23/58 208/138 |
| 2017/0095797 A1 | | 4/2017 | Cabiac | |

FOREIGN PATENT DOCUMENTS

| | | |
|---|---|---|
| FR | 2458524 A1 | 1/1981 |
| FR | 2991197 A1 | 12/2013 |

OTHER PUBLICATIONS

Search Report in corresponding FR1661622 dated Aug. 9, 2017.

* cited by examiner

*Primary Examiner* — Jun Li
(74) *Attorney, Agent, or Firm* — Millen, White, Zelano and Branigan, P.C.

(57) ABSTRACT

A catalyst comprises an active phase constituted by palladium, and a porous support comprising at least one refractory oxide selected from the group constituted by silica, alumina and silica-alumina, in which:
- the palladium content in the catalyst is in the range 0.0025% to 1% by weight with respect to the total weight of catalyst;
- at least 80% by weight of the palladium is distributed in a crust at the periphery of the porous support, the thickness of said crust being in the range 25 to 450 µm;
- the specific surface area of the porous support is in the range 70 to 160 m²/g;
- the metallic dispersion D of the palladium is less than 20%.

13 Claims, No Drawings

SELECTIVE HYDROGENATION CATALYST FOR A C3 HYDROCARBON CUT

TECHNICAL FIELD

The selective hydrogenation process can be used to transform the polyunsaturated compounds of oil cuts by conversion of the most unsaturated compounds into the corresponding alkenes, avoiding complete saturation and thus the formation of the corresponding alkanes.

The aim of the invention is to propose a catalyst with improved performances as well as a mode for the preparation of this catalyst, with this catalyst performing very well in processes for the selective hydrogenation of unsaturated hydrocarbon compounds present in C3 hydrocarbon cuts from steam cracking and/or from catalytic cracking.

PRIOR ART

Catalysts for the selective hydrogenation of C3 cuts from steam cracking and/or catalytic cracking are generally based on palladium, in the form of small metallic particles deposited on a support which may be a refractory oxide. The palladium content and the size of the particles of palladium are some of the criteria which are important as regards the activity and selectivity of the catalysts.

The macroscopic distribution of the metallic particles in the support also constitutes an important criterion, principally in the context of rapid and consecutive reactions such as selective hydrogenations. Generally, these elements have to be located in a crust at the periphery of the support in order to avoid problems with intragranular material transfer which could lead to defective activity and a loss of selectivity. As an example, the document US2006/025302 describes a catalyst for the selective hydrogenation of acetylene and diolefins, comprising palladium distributed in a manner such that 90% of the palladium is introduced into the catalyst in a crust of less than 250 μm.

Furthermore, in order to improve the selectivity of selective hydrogenation catalysts, and in particular of selective hydrogenation catalysts for unsaturated hydrocarbon compounds present in the C3 hydrocarbon cuts from steam cracking and/or catalytic cracking, it has been proposed in the prior art to add a second metal selected from group IB, preferably silver, in order to obtain bimetallic palladium-silver (Pd—Ag) catalysts. Catalysts of this type have been described in the documents FR 2 882 531 and FR 2 991 197. Adding silver to the active phase of the catalyst has the principal effect of reducing the metallic dispersion of the palladium but, in contrast, does not change the distribution of the particle sizes in the catalyst.

The Applicant has surprisingly discovered that the performances of a palladium catalyst, with part of the palladium being distributed in a crust at the periphery of the support, can be significantly improved in a process for the selective hydrogenation of unsaturated hydrocarbon compounds present in the C3 hydrocarbon cuts from steam cracking and/or catalytic cracking when said catalyst comprises an active phase constituted solely by palladium, i.e. it does not include any metal, in particular silver, other than palladium in the active phase, said catalyst having a metallic dispersion of the palladium of less than 20%, with a palladium content and a porous support with a specific surface area which are well specified. Such a catalyst has been able to be obtained by a preparation process comprising a step for colloidal impregnation as well as a specific hydrothermal treatment step, bringing about sintering of the catalyst, having the effect of reducing the metallic dispersion of the palladium in the catalyst and unexpectedly resulting in obtaining a catalyst with enhanced performances in terms of selectivity.

In fact, the catalyst in accordance with the invention has a high selectivity, enabling a hydrogenation of acetylenic and/or allenic and/or diolefinic compounds to be carried out while limiting the total hydrogenation of the mono-olefins (propane in the case of C3 cuts) and limiting any oligomerization or polymerization reactions bringing about a reduction in the propylene yield and early deactivation of the catalyst.

Aims of the Invention

In a first aspect, the invention concerns a catalyst comprising an active phase constituted by palladium, and a porous support comprising at least one refractory oxide selected from the group constituted by silica, alumina and silica-alumina, in which:
- the palladium content in the catalyst is in the range 0.0025% to 1% by weight with respect to the total weight of catalyst;
- at least 80% by weight of the palladium is distributed in a crust at the periphery of the porous support, the thickness of said crust being in the range 25 to 450 μm;
- the specific surface area of the porous support is in the range 70 to 160 $m^2/g$;
- the metallic dispersion D of the palladium is less than 20%.

Preferably, the metallic dispersion D of the palladium is 18% or less.

Advantageously, the palladium content in the catalyst is in the range 0.025% to 0.8% by weight with respect to the total weight of catalyst.

Preferably, the specific surface area of the porous support is in the range 70 to 150 $m^2/g$.

Advantageously, at least 80% by weight of the palladium is distributed in a crust at the periphery of the porous support, the thickness of said crust being in the range 50 to 450 μm.

Preferably, the porous support is alumina.

Advantageously, the total pore volume of the support is in the range 0.1 to 1.5 $cm^3/g$.

Preferably, the porous support comprises in the range 0.0050% to 0.25% by weight of sulphur with respect to the total weight of catalyst.

Advantageously, the palladium is in the form of particles with a mean size in the range 4 to 10 nm.

In a further aspect, a process for the preparation of a catalyst in accordance with the invention comprises the following steps:
a) preparing a colloidal suspension of palladium oxide or palladium hydroxide in an aqueous phase by mixing an aqueous solution (I) comprising at least one hydroxide selected from the group constituted by alkali hydroxides and alkaline-earth hydroxides and an aqueous solution (II) comprising at least one precursor of palladium;
b) impregnating said solution obtained from step a) onto a porous support comprising at least one refractory oxide selected from the group constituted by silica, alumina and silica-alumina;
c) optionally, maturing the impregnated porous support obtained in step b) in order to obtain a catalyst precursor;
d) drying the catalyst precursor obtained in step b) or c) at a temperature in the range 70° C. to 200° C.;
e) optionally, calcining the dried catalyst obtained in step d) at a temperature in the range 250° C. to 900° C.;

f) carrying out a hydrothermal treatment of the dried catalyst obtained in step d) or of the calcined catalyst obtained in step e) at a temperature in the range 500° C. to 900° C., in air comprising in the range 150 to 5000 grams of water per kg of air;

g) optionally, carrying out a reduction treatment on the catalyst obtained at the end of step f) by contact with a reducing gas.

Advantageously, in step a), the palladium precursor is selected from the group constituted by palladium chloride, palladium nitrate and palladium sulphate.

Advantageously, in step f), a hydrothermal treatment of the dried catalyst obtained in step d) or of the calcined catalyst obtained in step e) is carried out at a temperature in the range 600° C. to 800° C., in air comprising 300 to 4500 grams of water per kg of air.

In a further aspect, a process for selective hydrogenation comprises bringing a C3 cut from steam cracking and/or catalytic cracking into contact with the catalyst in accordance with the invention or prepared in accordance with the invention, in which the temperature is in the range 0° C. to 300° C., at a pressure in the range 0.1 to 10 MPa, with a molar ratio of hydrogen/(polyunsaturated compounds to be hydrogenated) in the range 0.1 to 10 and at an hourly space velocity, HSV, in the range 0.1 to 100 $h^{-1}$ for a process carried out in the liquid phase, with a molar ratio of hydrogen/(polyunsaturated compounds to be hydrogenated) in the range 0.5 to 1000 and at an hourly space velocity, HSV, in the range 100 to 40000 $h^{-1}$ for a process carried out in the gas phase.

DETAILED DESCRIPTION OF THE INVENTION

Hereinbelow, the groups of the chemical elements are provided in accordance with the CAS classification (CRC Handbook of Chemistry and Physics, published by CRC press, Editor-in-chief D. R. Lide, $81^{st}$ edition, 2000-2001). As an example, group IB in the CAS classification corresponds to metals from column 11 of the new IUPAC classification.

1. Definitions

Metallic Dispersion of Particles (D)

The particle dispersion is a dimensionless quantity, often expressed as a percentage. The dispersion becomes larger as the particles become smaller. It is defined in the publication by R. Van Hardeveld and F. Hartog, "*The statistics of surface atoms and surface sites on metal crystals*", Surface Science 15, 1969, 189-230.

Definition of Palladium Crust Thickness

In order to analyse the distribution of the metallic phase on the support, a crust thickness is measured by Castaing microprobe (or electronic microprobe microanalysis). The instrument used is a CAMECA SX100, equipped with four crystal monochromators in order to analyse four elements simultaneously. The technique for analysis using the Castaing microprobe consists of detecting of X-rays emitted by a solid after excitation of its elements using a high energy electron beam. For the purposes of this characterization, the grains of catalyst are embedded in epoxy resin blocks. These blocks are polished until the section with the diameter of the beads or extrudates is obtained, then metallized by depositing carbon in a metallic evaporator. The electronic probe is scanned along the diameter of five beads or extrudates in order to obtain the mean distribution profile of the constituent elements of the solids.

When the palladium is distributed in the form of a crust, its local concentration generally reduces steadily when it is measured, starting from the edge of the catalytic grain towards the interior. A distance from the grain edge at which the local palladium content becomes zero often cannot be determined with reproducible precision. In order to measure a crust thickness which is significant for the majority of the palladium particles, the crust thickness is defined as the distance to the grain edge containing 80% by weight of the palladium.

It is defined in the publication by L. Sorbier et al. "Measurement of palladium crust thickness on catalyst by EPMA", Materials Science and Engineering 32 (2012). Starting from the distribution profile obtained using the Castaing microprobe (c(x)), it is possible to calculate the cumulative quantity Q(y) of palladium in the grain as a function of the distance y to the edge of a grain with radius r.

For a bead (i.e. for grains of catalyst which are not in accordance with the invention):

$$Q(y)=\int_{-r}^{-y} c(x)4\pi \cdot x^2 dx + \int_{y}^{r} c(x)4\pi \cdot x^2 dx$$

For an extrudate:

$$Q(y)=\int_{-r}^{-r+y} c(x)2\pi \cdot x dx + \int_{r-y}^{r} c(x)2\pi \cdot x dx$$

where r: radius of grain;
y: distance to edge of grain;
x: integration variable (position on the profile).

It is assumed that the concentration profile follows the diameter from x=−r to x=+r (x=0 being the centre). Q(r) then corresponds to the total quantity of the element in the grain. The following equation is then solved numerically for y:

$$\frac{Q(y)}{Q(r)} = 0.8$$

where c is a strictly positive function, Q is then a strictly increasing function and this equation has a unique solution which is the thickness of the crust.

2. Catalyst

The invention concerns a catalyst comprising an active phase constituted by palladium, and a porous support comprising at least one refractory oxide selected from the group constituted by silica, alumina and silica-alumina, in which:
- the palladium content in the catalyst is in the range 0.0025% to 1% by weight with respect to the total weight of catalyst, preferably in the range 0.025% to 0.8% by weight, and more preferably in the range 0.1% to 0.75% by weight;
- at least 80% by weight of the palladium is distributed in a crust at the periphery of the porous support, the thickness of said crust being in the range 100 to 450 µm, preferably in the range 125 to 300 µm, more preferably in the range 125 to 250 µm, and yet more preferably in the range 125 to 225 µm;
- the specific surface area of the porous support is in the range 70 to 160 $m^2/g$, preferably in the range 70 to 150 $m^2/g$, and more preferably in the range 80 to 140 $m^2/g$;

the metallic dispersion D of the palladium is less than 20%, preferably 18% or less.

The mean particle size for the palladium is in the range 4 to 10 nm, preferably in the range 3 to 6 nm. The mean crystallite size is deduced from measurements for the metallic dispersion of the particles (D), by applying the dispersion-particle size relationships which are known to the person skilled in the art and described in "Analyse physico-chimiques des catalyseurs industriels" [Physico-chemical analyses of industrial catalysts], Chapter I, Technip Publications, Paris, 2001.

The porous support is selected from the group constituted by silica, alumina and silica-alumina. More preferably, the support is alumina. The alumina may be present in any of the possible crystallographic forms: alpha, delta, theta, chi, gamma, etc, alone or as a mixture. Preferably, the support is selected from alpha, delta and theta alumina. More preferably, alpha alumina is selected.

The specific surface area of the porous support is in the range 70 to 160 m$^2$/g, preferably in the range 70 to 150 m$^2$/g, and more preferably in the range 80 to 140 m$^2$/g. The BET specific surface area is measured by nitrogen physisorption. The BET specific surface area is measured by nitrogen physisorption in accordance with the ASTM standard D3663-03 as described by Rouquerol F.; Rouquerol J.; Singh K. in "Adsorption by Powders & Porous Solids: Principle, methodology and applications", Academic Press, 1999.

The total pore volume of the support is in the range 0.1 to 1.5 cm$^3$/g, preferably in the range 0.2 to 1.4 cm$^3$/g, and more preferably in the range 0.25 to 1.3 cm$^3$/g. The total pore volume is measured by mercury porosimetry in accordance with the ASTM standard D4284-92, with a wetting angle of 140°, for example using an Autopore® III model instrument from Micromeritics®.

In one embodiment of the invention, the support for the selective hydrogenation catalyst is purely mesoporous, i.e. it has a pore diameter in the range 2 to 50 nm, preferably in the range 5 to 30 nm and more preferably in the range 8 to 20 nm.

In another embodiment in accordance with the invention, the selective hydrogenation catalyst support is bimodal, the first mode being mesoporous, i.e. with a pore diameter in the range 2 to 50 nm, preferably in the range 5 to 30 nm and more preferably in the range 8 to 20 nm, and the second being macroporous, i.e. with pores with a diameter of more than 50 nm. Said support advantageously has a pore volume for pores with a pore diameter in the range 50 to 700 nm of less than 20% of the total pore volume of the support, preferably less than 18% of the total pore volume of the support and particularly preferably less than 15% of the total pore volume of the support.

The support may optionally comprise sulphur. The sulphur content in the support may be in the range 0.0050% to 0.25% by weight with respect to the total weight of catalyst, preferably in the range 0.0075% to 0.20% by weight.

In accordance with the invention, the porous support is in the form of beads, trilobes, extrudates, pellets or irregular and non-spherical agglomerates the specific shape of which may be the result of a crushing step. Highly advantageously, the support is in the form of beads or extrudates. Yet more advantageously, the support is in the form of beads. The diameter of the beads is in the range 1 mm to 10 mm, preferably in the range 2 to 8 mm, and more preferably in the range 2 to 6 mm.

3. Preparation Process

The invention also concerns a process for the preparation of the catalyst. The solution of palladium may be deposited onto the support using any of the techniques known to the person skilled in the art. Preferably, the palladium solution is deposited using a colloidal method.

More particularly, the process for the preparation of the catalyst in accordance with the invention in general comprises the following steps:

a) preparing a colloidal suspension of palladium oxide or palladium hydroxide in an aqueous phase by mixing an aqueous solution (I) comprising at least one hydroxide selected from the group constituted by alkali hydroxides and alkaline-earth hydroxides and an aqueous solution (II) comprising at least one precursor of palladium;

b) impregnating said colloidal suspension obtained from step a) onto a porous support comprising at least one refractory oxide selected from the group constituted by silica, alumina and silica-alumina;

c) optionally, maturing the impregnated porous support obtained in step b) in order to obtain a catalyst precursor;

d) drying the catalyst precursor obtained in step b) or c) at a temperature in the range 70° C. to 200° C.;

e) optionally, calcining the dried catalyst obtained in step d) at a temperature in the range 250° C. to 900° C.;

f) carrying out a hydrothermal treatment of the dried catalyst obtained in step d) or of the calcined catalyst obtained in step e) at a temperature in the range 500° C. to 900° C., in air comprising in the range 150 to 5000 grams of water per kg of air;

g) optionally, carrying out a reduction treatment on the calcined catalyst obtained at the end of step f) by contact with a reducing gas.

The various steps are explained in detail below.

a) Preparation of a Colloidal Suspension of Palladium Oxide or Palladium Hydroxide in an Aqueous Phase The colloidal suspension is generally obtained by hydrolysis of the palladium cation in an aqueous medium, which results in the formation of particles of palladium oxide or hydroxide in suspension.

The aqueous solution of alkali hydroxides or alkaline-earth hydroxides is generally selected from the group constituted by aqueous solutions of sodium hydroxide, aqueous solutions of magnesium hydroxide. Preferably, the aqueous solution is by preference an aqueous solution of sodium hydroxide.

The palladium precursor salt is generally selected from the group constituted by palladium chloride, palladium nitrate and palladium sulphate. Highly preferably, the precursor salt of palladium is palladium nitrate.

Typically, the aqueous solution comprising at least one precursor salt of palladium [hereinafter also termed solution (II)] is supplied to a suitable apparatus, followed by the aqueous solution comprising at least one alkali hydroxide or alkaline-earth hydroxide [hereinafter also termed solution (I)]. Alternatively, the solutions (I) and (II) may be poured into the apparatus simultaneously. Preferably, the aqueous solution (II) is poured into the apparatus, followed by the aqueous solution (I).

The colloidal suspension generally remains in the apparatus for a dwell time in the range 0 to 20 hours.

The concentrations of the solutions (I) and (II) are generally selected in order to obtain a pH of the colloidal suspension in the range 1.0 to 3.5. Thus, the pH of the colloidal suspension may be modified during this dwell time by adding quantities of acid or base compatible with the stability of the colloidal suspension.

In general, the preparation temperature is in the range 5° C. to 40° C., and preferably in the range 15° C. to 35° C.

The concentration of palladium is preferably in the range 5 to 150 millimoles per litre (mmol/L), more preferably in the range 8 to 80 millimoles per litre.

b) Depositing the Colloidal Suspension Prepared in Step a) by Impregnation onto a Support, Preferably onto Alumina The colloidal suspension prepared in step 1a) is then impregnated onto a support.

The support may optionally undergo a series of treatments before the impregnation step, such as calcining or hydration treatments. The support may also already comprise one or more metallic elements before impregnation of the colloidal suspension. Metallic elements may also be introduced into the colloidal suspension. These metallic elements may be introduced either by conventional techniques, or by using the process in accordance with the present invention.

The colloidal suspension is preferably poured onto the support. Preferably, the volume of the colloidal suspension impregnated onto the support is in the range 0.9 to 1.1 times the pore volume. This process may be carried out either in a batchwise manner, i.e. the step for preparation of the colloidal suspension precedes the step for impregnation onto the support and that the main part of the colloidal suspension is sent to the impregnation step all at once, or continuously, i.e. the product obtained from step a) is sent continuously to step b) after adjusting the dwell time of the colloidal suspension.

A process in which the solutions (I) and (II) are poured simultaneously into a tank which continuously overflows into a zone comprising the support to be impregnated may be mentioned as an example of a continuous process.

c) Maturation of Support Impregnated During Step b) for a Period in the Range 0.5 to 40 Hours (Optional Step)

After impregnation, the impregnated support is generally matured in the moist state for 0.5 to 40 h, preferably for 1 to 30 h. Longer durations are not excluded, but do not necessarily result in an improvement.

d) Drying the Catalyst Precursor Obtained from Step b) or c)

The catalyst precursor is generally dried in order to eliminate all or a portion of the water introduced during impregnation, preferably at a temperature in the range 50° C. to 250° C., more preferably in the range 70° C. to 200° C. The drying period is in the range 0.5 h to 20 h. Longer durations are not excluded, but do not necessarily result in an improvement.

Drying is generally carried out in air from the combustion of a hydrocarbon, preferably methane, or in heated air comprising between 0 and 80 grams of water per kilogram of combustion air, an oxygen content in the range 5% to 25% by volume and a carbon dioxide content in the range 0 to 10% by volume.

e) Calcining the Dried Catalyst Obtained from Step d) in Combustion Air (Optional Step)

After drying, the catalyst may be calcined in air, preferably in combustion air, and more preferably air from the combustion of methane comprising between 40 and 80 grams of water per kg of air, an oxygen content in the range 5% to 15% by volume and a $CO_2$ content in the range 4% to 10% by volume. The calcining temperature is generally in the range 250° C. to 900° C., preferably in the range from approximately 300° C. to approximately 500° C. The calcining period is generally in the range 0.5 h to 5 h.

f) Hydrothermal Treatment of Dried Catalyst Obtained from Step d) or Calcined Catalyst Obtained from Step e)

After the drying step d) or the calcining step e), the catalyst undergoes a hydrothermal treatment in air, preferably in combustion air comprising in the range 150 to 5000 grams of water per kg of air, preferably in the range 300 to 4500, and more preferably in the range 500 to 4000 grams of water per kg of air.

The temperature of the hydrothermal treatment is in the range 500° C. to 900° C., preferably in the range 600° C. to 700° C.

The duration of the hydrothermal treatment is generally in the range 0.5 to 5 hours.

g) Reduction of Supported Oxide Obtained from Step f), Preferably Using Gaseous Hydrogen (Optional Step)

The catalyst is generally reduced. This step is preferably carried out in the presence of a reducing gas, either in situ, i.e. in the reactor in which the catalytic transformation is being carried out, or ex situ. Preferably, this step is carried out at a temperature in the range 80° C. to 180° C., more preferably in the range 100° C. to 160° C.

The reduction is carried out in the presence of a reducing gas comprising between 25% by volume and 100% by volume of hydrogen, preferably 100% by volume of hydrogen. The hydrogen is optionally supplemented by a gas which is inert to reduction, preferably argon, nitrogen or methane.

The reduction generally comprises a temperature rise phase followed by a constant temperature stage.

The duration of the constant temperature stage for reduction is generally in the range 1 to 10 hours, preferably in the range 2 to 8 hours.

The hourly space velocity (HSV) is generally in the range 150 to 3000, preferably in the range 300 to 1500 litres of reducing gas per hour and per litre of catalyst.

Use of the Catalyst

The catalyst in accordance with the invention may be used in processes for the selective hydrogenation of unsaturated hydrocarbon compounds present in the C3 hydrocarbon cuts from steam cracking and/or catalytic cracking. The selective hydrogenation process in accordance with the invention is intended to eliminate said polyunsaturated hydrocarbons present in said feed to be hydrogenated without hydrogenating the mono-unsaturated hydrocarbons. More particularly, the selective hydrogenation process in accordance with the invention is intended to selectively hydrogenate propadiene and methylacetylene.

Thus, for example, the C3 steam cracking cut may have the following mean composition: of the order of 90% by weight of propylene, of the order of 3% to 8% by weight of propadiene and methylacetylene, the rest being essentially propane.

In some C3 cuts, between 0.1% and 2% by weight of C2 and C4 may also be present. The specifications concerning the concentrations of these polyunsaturated compounds for petrochemicals and polymerization units are very low: 20-30 ppm by weight of MAPD (methylacetylene and propadiene) and more than 95% of propylene for chemical quality propylene and less than 10 ppm by weight or even down to 1 ppm by weight for "polymerization" quality and more than 99% propylene.

The technology used for the selective hydrogenation process involves, for example, injecting polyunsaturated hydrocarbon feed and hydrogen into at least one fixed bed reactor as an upflow or downflow. Said reactor may be of the isothermal or adiabatic type. An adiabatic reactor is preferred. The polyunsaturated hydrocarbon feed may advantageously be diluted with one or more re-injection(s) of effluent obtained from said reactor in which the selective hydrogenation reaction is carried out, to various points of the reactor located between the inlet and outlet of the reactor in order to limit the temperature gradient in the reactor. The technology of the selective hydrogenation process in accordance with the invention may also advantageously involve installing at least said supported catalyst in a reactive distillation column or in exchanger-reactors. The stream of hydrogen may be introduced at the same time as the feed to be hydrogenated and/or at one or more different points of the reactor.

Selective hydrogenation of the C3 cuts may be carried out in the gas phase or in the liquid phase, preferably in the liquid phase. A liquid phase reaction can be used to reduce energy costs and increase the cycle time for the catalyst.

In general, the selective hydrogenation of C3 cuts is carried out at a temperature in the range 0° C. to 300° C., preferably in the range 20° C. to 100° C., at a pressure in the range 0.1 to 10 MPa, preferably in the range 0.5 to 5 MPa, at a molar ratio of hydrogen/(polyunsaturated compounds to be hydrogenated) in the range 0.1 to 10 and at an hourly space velocity HSV (defined as the ratio of the volume flow rate of feed to the volume of catalyst) in the range 0.1 to 100 $h^{-1}$ for a process carried out in the liquid phase, with a molar ratio of hydrogen/(polyunsaturated compounds to be hydrogenated) in the range 0.5 to 1000 and at an hourly space velocity HSV in the range 100 to 40000 $h^{-1}$ for a process carried out in the gas phase.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding application No. FR 1661622, filed Nov. 29, 2016 are incorporated by reference herein.

EXAMPLES

The examples presented below are intended to demonstrate the improvement in catalytic activity for selective hydrogenation with the catalysts in accordance with the invention. Examples 1 to 4 concern processes for the preparation of catalysts which are not in accordance with the invention (catalysts C1 to C4), and Examples 5 and 6 concern processes for the preparation of a catalyst in accordance with the invention (catalysts C5 and C6).

Example 7 concerns the measurement of the metallic dispersion D of catalysts C1 to C6.

Example 8 concerns the application of these catalysts in a selective hydrogenation reaction for a C3 cut.

These examples are presented by way of illustration and do not in any way limit the scope of the invention.

Example 1: Preparation of a Catalyst C1, not in Accordance with the Invention

A colloidal suspension of Pd oxide was prepared, with stirring at 25° C., by diluting 1.8 g of a solution of palladium nitrate $Pd(NO_3)_2$ containing 8.5% by weight of palladium Pd with approximately 45 mL of demineralized water, then adding approximately 10 mL of a sodium hydroxide solution in order to obtain a pH of 2.4. The suspension was then diluted with demineralized water to a volume which corresponded to the pore volume of the alumina support. This solution was then impregnated onto 80 g of an alumina with a specific surface area of 71 $m^2/g$, shaped into the form of beads. A step for maturation of the impregnated support, before drying, for a period of 3 h was carried out in air in a confined, moist medium. The solid obtained was dried in air for 20 h at 120° C.

The catalyst C1 was dried in air at 120° C., then calcined for 2 hours at 450° C. in a stream of combustion air with a HSV of 500 litres of combustion air per litre of catalyst and per hour. The combustion air contained approximately 60 g of water per kilogram of dry air.

The catalyst C1 prepared in this manner comprised 0.19% by weight of palladium with respect to the total weight of catalyst.

Characterization of catalyst C1 by Castaing microprobe showed that 80% of the Pd was distributed in a crust with a thickness of approximately 222 μm.

The metallic dispersion D of the palladium of catalyst C1 was 26%.

Example 2: Preparation of a Catalyst C2, not in Accordance with the Invention

A colloidal suspension of Pd oxide was prepared, with stirring at 25° C., by diluting 1.8 g of a solution of palladium nitrate $Pd(NO_3)_2$ containing 8.5% by weight of palladium Pd with approximately 45 mL of demineralized water, then adding approximately 10 mL of a sodium hydroxide solution in order to obtain a pH of 2.4. The suspension was then diluted with demineralized water to a volume which corresponded to the pore volume of the alumina support. This solution was then impregnated onto 80 g of an alumina with a specific surface area of 71 $m^2/g$, shaped into the form of beads. A step for maturation of the impregnated support, before drying, for a period of 3 h was carried out in air in a confined, moist medium. The solid obtained was dried in air for 20 h at 120° C.

The catalyst C2 was dried in air at 120° C., then calcined for 2 hours at 650° C. in a stream of combustion air with a HSV of 4000 litres of combustion air per litre of catalyst and per hour. The combustion air contained approximately 60 g of water per kilogram of dry air.

The catalyst C2 prepared in this manner comprised 1.5% by weight of palladium with respect to the total weight of catalyst.

Characterization of catalyst C2 by Castaing microprobe showed that 80% of the Pd was distributed in a crust with a thickness of approximately 500 μm.

The metallic dispersion D of the palladium of catalyst C2 was 25%.

Example 3: Preparation of a Catalyst C3, not in Accordance with the Invention (Dry Impregnation Method)

An aqueous solution of palladium nitrate was prepared at 25° C. by diluting 3.5 g of a solution of palladium nitrate containing 8.5% by weight of palladium with demineralized water to a volume which corresponded to the pore volume of the alumina support.

This solution was then impregnated (using the dry impregnation method) onto 100 grams of an alumina which had a $S_{BET}$ of 300 $m^2/g$. This alumina was in the form of beads which had a mean diameter of 3 mm.

A step for maturation of the impregnated support before drying for a period of 20 h was carried out in air in a confined and moist medium. The solid obtained was dried in air for 2 h at 120° C. The catalyst 1 obtained was dried in air at 120° C., then calcined for 2 hours at 650° C. in a stream of combustion air with a HSV of 3000 litres of combustion air per litre of catalyst per hour. The combustion air contained approximately 4000 g of water per kg of dry air.

The catalyst C3 prepared in this manner comprised 0.19% by weight of palladium with respect to the total weight of catalyst.

Characterization of catalyst C3 by Castaing microprobe showed that 80% of the Pd was distributed in a crust with a thickness of approximately 500 μm.

The metallic dispersion D of the palladium of catalyst C3 was 30%.

Example 4: Preparation of a Catalyst C4, not in Accordance with the Invention

A colloidal suspension of Pd oxide was prepared, with stirring at 25° C., by diluting 1.8 g of a solution of palladium nitrate $Pd(NO_3)_2$ containing 8.5% by weight of palladium Pd with approximately 45 mL of demineralized water, then adding approximately 10 mL of a sodium hydroxide solution in order to obtain a pH of 2.4. The suspension was then diluted with demineralized water to a volume which corresponded to the pore volume of the alumina support. This solution was then impregnated onto 80 g of an alumina with a specific surface area of 300 $m^2$/g, shaped into the form of beads. A step for maturation of the impregnated support, before drying, for a period of 3 h was carried out in air in a confined, moist medium.

The catalyst 4 obtained was dried in air at 120° C., then calcined for 2 hours at 650° C. in a stream of combustion air with a HSV of 500 litres of combustion air per litre of catalyst and per hour. The combustion air contained approximately 4000 g of water per kg of air.

The catalyst C4 prepared in this manner comprised 0.18% by weight of palladium with respect to the total weight of catalyst.

Characterization of catalyst C4 by Castaing microprobe showed that 80% of the Pd was distributed in a crust with a thickness of approximately 210 μm.

The metallic dispersion D of the palladium of catalyst C4 was 23%.

Example 5: Preparation of a Catalyst C5, in Accordance with the Invention

A colloidal suspension of Pd oxide was prepared, with stirring at 25° C., by diluting 1.8 g of a solution of palladium nitrate $Pd(NO_3)_2$ containing 8.5% by weight of palladium Pd with approximately 45 mL of demineralized water, then adding approximately 10 mL of a sodium hydroxide solution in order to obtain a pH of 2.4. The suspension was then diluted with demineralized water to a volume which corresponded to the pore volume of the alumina support. This solution was then impregnated onto 80 g of an alumina with a specific surface area of 90 $m^2$/g, shaped into the form of beads. A step for maturation of the impregnated support, before drying, for a period of 3 h was carried out in air in a confined, moist medium.

The catalyst C5 obtained was dried in air at 120° C., then calcined for 2 hours at 650° C. in a stream of combustion air with a HSV of 500 litres of combustion air per litre of catalyst and per hour. The combustion air contained approximately 3500 g of water per kg of air.

The catalyst C5 prepared in this manner comprised 0.18% by weight of palladium with respect to the total weight of catalyst.

Characterization of catalyst C5 by Castaing microprobe showed that 80% of the Pd was distributed in a crust with a thickness of approximately 195 μm.

The metallic dispersion D of the palladium of catalyst C5 was 14%.

Example 6: Preparation of a Catalyst C6, in Accordance with the Invention

A colloidal suspension of Pd oxide was prepared, with stirring at 25° C., by diluting 1.8 g of a solution of palladium nitrate $Pd(NO_3)_2$ containing 8.5% by weight of palladium Pd with approximately 45 mL of demineralized water, then adding approximately 10 mL of a sodium hydroxide solution in order to obtain a pH of 2.4. The suspension was then diluted with demineralized water to a volume which corresponded to the pore volume of the alumina support. This solution was then impregnated onto 80 g of an alumina with a specific surface area of 150 $m^2$/g, shaped into the form of beads. A step for maturation of the impregnated support, before drying, for a period of 3 h was carried out in air in a confined, moist medium.

The catalyst 6 obtained was dried in air at 120° C., then calcined for 2 hours at 650° C. in a stream of combustion air with a HSV of 500 litres of combustion air per litre of catalyst and per hour. The combustion air contained approximately 3500 g of water per kg of air.

The catalyst C6 prepared in this manner comprised 0.30% by weight of palladium with respect to the total weight of catalyst.

Characterization of catalyst C6 by Castaing microprobe showed that 80% of the Pd was distributed in a crust with a thickness of approximately 150 μm.

The metallic dispersion D of the palladium of catalyst C6 was 12%.

Example 7: Measurement of Metallic Dispersion D of Catalysts C1 to C6

The measurements of the metallic dispersions were carried out by chemisorption of carbon monoxide CO onto the catalyst which had been reduced under 1 litre of hydrogen per hour and per gram of catalyst, with a temperature ramp-up of 300° C./h and a two hour constant temperature stage at 150° C. The catalyst was then flushed for 1 hour at 150° C. under helium then cooled to 25° C. under helium.

The CO chemisorption was carried out dynamically at 25° C. in accordance with the usual practices known to the person skilled in the art, resulting in a volume of chemisorbed CO from which the person skilled in the art could calculate the number of chemisorbed CO molecules. A stoichiometric ratio of one molecule of CO per atom of Pd on the surface was assumed in order to calculate the number of Pd atoms on the surface. The dispersion is expressed as the % of surface Pd atoms with respect to all of the Pd atoms present in the catalyst sample. The metallic dispersion D for the palladium of the catalysts C1 to C6 is presented in Table 1 below.

TABLE 1

Metallic dispersion D of catalysts C1 to C6

| | $S_{BET}$ support $(m^2/g)$ | Pd content (% by wt) | Impregnation method | Hydrothermal treatment | Dispersion (%) | Size of crust (μm) |
|---|---|---|---|---|---|---|
| C1 (not in accordance) | 71 | 0.19 | colloidal | 450° C./60 g of water* | 26 | 222 |
| C2 (not in accordance) | 71 | 1.5 | colloidal | 650° C./60 g of water* | 25 | 500 |
| C3 (not in accordance) | 300 | 0.19 | Dry impregnation | 650° C./4000 g of water* | 30 | 500 |
| C4 (not in accordance) | 300 | 0.18 | colloidal | 650° C./4000 g of water* | 23 | 210 |
| C5 (in accordance) | 90 | 0.18 | colloidal | 650° C./3500 g of water* | 14 | 195 |
| C6 (in accordance) | 150 | 0.30 | colloidal | 650° C./3500 g of water* | 12 | 150 |

*per kg of dry air

Example 8: Use of Catalysts C1 to C6 for the Selective Hydrogenation of the C3 Steam Cracking Cut A feed comprising 92.47% by weight of propylene, 4.12% by weight of propane, 1.18% by weight of methylacetylene (MA), 1.63% by weight of propadiene (PD) was treated with catalysts C1 to C7. Before the reaction, the selective hydrogenation catalysts were activated in a stream of hydrogen at 160° C. for 2 h.

25 mL of catalyst was placed in a tube reactor in upflow mode. The pressure was maintained at 30 bar (3 MPa) and the temperature was held at 27° C. An hourly space velocity (HSV) of 50 h$^{-1}$ was applied. The H$_2$/MAPD molar ratio was varied between 0, 5, 10 mol/mol. The composition of the feed and of the effluent was measured continuously at the reactor outlet by gas phase chromatography. The gaseous oligomers were defined as the oligomers not trapped by the various filters of the unit and detected by the chromatographic column (composed of up to 6 carbons). The performances of the catalysts C1 to C6 are recorded in Table 2 below.

TABLE 2

Selectivities measured for the selective hydrogenation of the C3 cut

| Catalyst | Propylene selectivity for a conversion of 90% of MAPD* (%) | Gaseous oligomers selectivity for a conversion of 90% of MAPD* (%) |
|---|---|---|
| C1 (not in accordance) | 52 | 13 |
| C2 (not in accordance) | 55 | 14 |
| C3 (not in accordance) | 62 | 18 |
| C4 (not in accordance) | 60 | 14 |
| C5 (in accordance) | 64 | 6 |
| C6 (in accordance) | 71 | 4 |

*MAPD = methylacetylene and propadiene

The catalysts C5 and C6 were in accordance with the invention. They both had a very good selectivity for propylene and for the production of gaseous oligomers. The most selective catalysts are those which have a thin palladium crust, i.e. less than 450 microns, as well as a dispersion of less than 20%.

These catalysts were prepared on supports having a specific surface area of more than 70 m$^2$/g and less than 160 m$^2$/g because beyond this, the acidity of the support catalyses the oligomerization reaction, as illustrated in Example 4 in which the catalyst C4 generated a large quantity of oligomers, leading to early coking of the catalyst and to a shorter service life for the latter. Specific surface areas which are too high and/or a palladium content which is too high as well as CO dispersions which are too high result in low performance catalysts C1 to C4, producing too much propane, a compound which is not wanted in this application, and gaseous oligomer contents which are symptomatic of the production of more oligomers and of too much coke, thereby compromising the service life of the catalyst and the proper operation of the hydrogenation unit.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A catalyst consisting of palladium, and a porous support comprising at least one refractory oxide that is silica, alumina or silica-alumina, in which:
    the palladium content in the catalyst is in the range 0.0025% to 1% by weight with respect to the total weight of catalyst;
    at least 80% by weight of the palladium is distributed in a crust at the periphery of the porous support, the thickness of said crust being in the range 125 to 225 μm;
    the specific surface area of the porous support is in the range 70 to 150 m$^2$/g;
    the metallic dispersion D of the palladium is less than 20%.

2. The catalyst as claimed in claim 1, in which the metallic dispersion D of the palladium is 18% or less.

3. The catalyst as claimed in claim 1, in which the palladium content in the catalyst is 0.025% to 0.8% by weight with respect to the total weight of catalyst.

4. The catalyst as claimed in claim 1, Therein the specific surface area of the porous support is 70 to 150 m$^2$/g.

5. The catalyst as claimed in claim 1, wherein at least 80% by weight of the palladium is distributed in a crust at the periphery of the porous support, the thickness of said crust being 50 to 450 μm.

6. The catalyst as claimed in claim 1, wherein the porous support is alumina.

7. The catalyst as claimed in claim 1, wherein the total pore volume of the support is in the range 0.1 to 1.5 cm³/g.

8. The catalyst as claimed in claim 1, wherein the porous support comprises in the range 0.0050% to 0.25% by weight of sulphur with respect to the total weight of catalyst.

9. The catalyst as claimed in claim 1, wherein the palladium is in the form of particles with a mean size in the range 4 to 10 nm.

10. A process for the preparation of a catalyst as claimed in claim 1, comprising:
   a) preparing a colloidal suspension of palladium oxide or palladium hydroxide in an aqueous phase by mixing an aqueous solution (I) comprising at least one alkali hydroxide or alkaline-earth hydroxide and an aqueous solution (II) comprising at least one precursor of palladium;
   b) impregnating said solution obtained from a) onto a porous support comprising at least one refractory oxide that is silica, alumina or silica-alumina;
   c) optionally, maturing the impregnated porous support obtained in b) in order to obtain a catalyst precursor;
   d) drying the catalyst precursor obtained in b) or c) at a temperature in the range 70° C. to 200° C.;
   e) optionally, calcining the dried catalyst obtained in d) at a temperature in the range 250° C. to 900° C.;
   f) carrying out a hydrothermal treatment of the dried catalyst obtained in d) or of the calcined catalyst obtained in e) at a temperature in the range 500° C. to 900° C., in air comprising in the range 150 to 5000 grams of water per kg of air;
   g) optionally, carrying out a reduction treatment on the catalyst obtained at the end of f) by contact with a reducing gas.

11. The preparation process as claimed in claim 10, in which in a), the palladium precursor is palladium chloride, palladium nitrate or palladium sulphate.

12. The process as claimed in claim 10, in which in f), a hydrothermal treatment of the dried catalyst obtained in d) or of the calcined catalyst obtained in e) is carried out at a temperature in the range 600° C. to 800° C., in air comprising 300 to 4500 grams of water per kg of air.

13. A process for selective hydrogenation, comprising bringing a C3 cut from steam cracking and/or catalytic cracking into contact with the catalyst as claimed in claim 1, in which the temperature is in the range 0° C. to 300° C., at a pressure in the range 0.1 to 10 MPa, with a molar ratio of hydrogen/(polyunsaturated compounds to be hydrogenated) in the range 0.1 to 10 and at an hourly space velocity, HSV, in the range 0.1 to 100 h$^{-1}$ for a process carried out in the liquid phase, with a molar ratio of hydrogen/(polyunsaturated compounds to be hydrogenated) in the range 0.5 to 1000 and at an hourly space velocity, HSV, in the range 100 to 40000 h$^{-1}$ for a process carried out in the gas phase.

* * * * *